(12) United States Patent
Back et al.

(10) Patent No.: US 7,084,322 B2
(45) Date of Patent: Aug. 1, 2006

(54) METHOD FOR BIOSYNTHESIZING THE SEROTONIN DERIVATIVES IN PLANTS

(75) Inventors: Kyoungwhan Back, Gwangju (KR); Sun-Mi Jang, Jeollanam-do (KR)

(73) Assignee: Chonnam National University (KR)

( * ) Notice: Subject to any disclaimer, the term of this patent is extended or adjusted under 35 U.S.C. 154(b) by 0 days.

(21) Appl. No.: 10/872,560

(22) Filed: Jun. 22, 2004

(65) Prior Publication Data

US 2004/0268437 A1 Dec. 30, 2004

(30) Foreign Application Priority Data

Jun. 24, 2003 (KR) .................. 10-2003-0041041
Dec. 19, 2003 (KR) .................. 10-2003-0093801

(51) Int. Cl.
*C12N 15/82* (2006.01)
*C12N 15/54* (2006.01)
*C12N 15/29* (2006.01)
*A01H 5/00* (2006.01)
*A01H 5/10* (2006.01)

(52) U.S. Cl. ................ 800/278; 800/317.1; 800/320.2; 435/193

(58) Field of Classification Search ................ 435/193, 435/419; 800/278, 320.2, 317.1, 306, 314, 800/315, 320
See application file for complete search history.

(56) References Cited

U.S. PATENT DOCUMENTS 5,451,514 A * 9/1995 Boudet et al. .............. 800/286

FOREIGN PATENT DOCUMENTS

KR      10-354791      5/2001

OTHER PUBLICATIONS

Walther, DJ and Bader, M. A unique central tryptophan hydroxylase isoform. 2003.□ □ Biochem Pharm. 66. pp. 1673-1680.*
Odjakova M and Hadjiivanova, C. Animal neurotransmitter substances in plants. 1997. Bulg. J. Plant Physiol. 23(1-2), pp. 94-102.*
Walden R and Schell J. Techniques in plant molecular biology- progress and problems. 1990. Eur. J. Biochem. 192, pp. 563-576.*
Phillips et al. Proc. Genetic Stability of plant tissue cultures: breakdown of normal controls. 1994. PNAS. USA. vol. 91 pp. 5222-5226.*
Hotta, et al., "Protective effects of antioxidative serotonin derivatives isolated from safflower against postischemic myocardial dysfunction", Molecular and Cellular Biochemistry 238, pp. 151-162, 2002.
Takii, et al., "Multiple mechanisms involved in the inhibition of proinflammatory cytokine production from human monocytes by N-(p-coumaroyl)serotonin and its derivatives", International Immunopharmacology 3, pp. 273-277, 2003.
Farmer, et al., "Identification and characterization of cDNA clones encoding hydroxycinnamoyl-CoA:tyramine N-hyroxycinnamoyltransferase from tobacco", Eur. J. Biochem. 263, pp. 686-694, 1999.
Tanaka et al., "Phenylpropanoid amides of serotonin accumulate in witches' broom diseased bamboo", Phytochemistry 64, pp. 965-969, 2003.
Lee, et al., "Transgenic Rice Plants Expressing a *Bacillus subtilis* Protoporphyinogen Oxidase Gene Are Resistant to Diphenyl Ether Herbicide Oxyfluorfen", Plant Cell Physiol. 41(6), pp. 743-749, 2000.
Back, et al., "Cloning and Characterization of a Hydroxycinnamoyl-CoA:Tyramine N-(Hydroxycinnamoyl) Transferase Induced in Response to UV-C and Wounding from *Capsicum annuum*", Plant Cell Physiol. 42(5), pp. 475-481, 2001.
Jang, et al., "Production of Coumaroylserotonin and Feruloylserotonin in Transgenic Rice Expressing Pepper Hydroxycinnamoyl-Coenzyme A:Serotonin N-(Hydroxycinnamoyl)transferase[1]", Plant Physiol. 135, pp. 346-356, 2004.
Ishihara, et al., "Induction of N-Hydroxycinnamoyltyramine Synthesis and Tyramine N-Hydroxycinnamoyltransferase (THT) Activity by Wounding in Maize Leaves", Biosci. Biotechnol. Bichem., 64(5), pp. 1025-1031, 2000.
Schmidt, et al., "Cloning and Expression of a Potato cDNA Encoding Hydroxycinnamoyl-CoA:Tyramine N-(Hydroxycinnamoyl) transferase", J. Biol. Chem. 274(7), pp. 4273-4280, 1999.
Schmidt, et al., "Elicitor-stimulated biosynthesis of hydroxycinnamoyltyramines in cell suspension cultures of *Solanum tuberosum*", Planta 205, pp. 51-55, 1998.

* cited by examiner

*Primary Examiner*—David T. Fox
(74) *Attorney, Agent, or Firm*—Buchanan Ingersoll PC

(57) ABSTRACT

The present invention relates to a method for biosynthesizing the serotonin derivatives in plants, more particularly, a method for biosynthesizing the serotonin derivatives characterized by treating plants with inducers for serotonin derivative biosynthesis or by inducing over-expression of tyramine N-(hydroxy cinnamoyl)transferase in plants. The method of the present invention facilitates the production of serotonin derivatives such as feruloylserotonin and coumaroylserotonin that have activities of anticancer, anti-oxidation and promoting bone-formation. The serotonin derivatives prepared by the method above can be used either after being purified or as edible plants themselves.

8 Claims, 5 Drawing Sheets

METHOD FOR BIOSYNTHESIZING THE SEROTONIN DERIVATIVES IN PLANTS

FIELD OF THE INVENTION

The present invention relates to a method for biosynthesizing the serotonin derivatives in plants, more particularly, a method for biosynthesizing the serotonin derivatives characterized by treating plants with inducers for serotonin derivative biosynthesis or by inducing over-expression of tyramine N-(hydroxy cinnamoyl)transferase in plants.

BACKGROUND OF THE INVENTION

The serotonin derivative is a kind of N-(hydroxycinnamoyl)-amines. The N-(hydroxycinnamoyl)-amines are conjugates of hydroxycinnamic acid derivatives and aromatic amines. Feruloyltyramine, feruloyloctopamine, 4-coumaroyltyramine, feruloyl-3'-methoxyoctopamine, 4-coumaroyloctopamine, feruloylserotonin and coumaroylserotonin are the representative compounds of N-(hydroxycinnamoyl)-amines. The N-(hydroxycinnamoyl)-amines such as feruloyltyramine and coumaroyltyramine are involved in the strengthening of a plant cell wall through peroxidative polymerization with proteins in a cell membrane and lignin, a component of a cell wall (Schmidt et al., Planta, 205, 51–55, 1998), after being introduced in a plant cell wall. The amount of the compound synthesized in a plant rapidly increases by an invasion of pathogenic bacteria or wounding (Fritzermeier et al., Plant Physiol. 85, 34–41, 1987; Joos et al., Eur. J. Biochem. 204, 621–629, 1992).

One constituent of the N-(hydroxycinnamoyl)-amines, hydroxycinnamic acid derivatives is synthesized through phenylpropanoid pathway. In other words, hydroxycinnamoyl-CoA is synthesized from hydroxycinnamate by hydroxycinnamate:CoA ligase using ATP and CoA-SH. Feruloyl-CoA, cinnamoyl-CoA, 4-coumaroyl-CoA and sinapoyl-CoA are the representative ones.

The other constituent of the N-(hydroxycinnamoyl)-amines, aromatic amines is synthesized through shikimate pathway. That is, aromatic amines are produced by decarboxylation of an amino acid by decarboxylase. And tyramine derived from tyrosine; serotonin derived from tryptophan; dopamine; noradrenaline; and octopamine are the representative ones.

N-(hydroxycinnamoyl)-amines are produced by conjugation of hydroxycinnamic acid derivatives synthesized through phenylpropanoid pathway and aromatic amines synthesized through shikimate pathway using N-(hydroxycinnamoyl)transferase.

The tyramine N-(hydroxycinnamoyl)transferase (referred to as 'THT' hereinafter) is an enzyme producing N-(hydroxycinnamoyl)-amines using various hydroxycinnamic acid derivatives and aromatic amines as substrates. At first, THT was purified by chromatography after treating potato culture cells with an elicitor prepared from *Phytophthora infestans* (Hohifeld et al., Plant Physiol. 107, 545–552, 1995). The molecular weight of potato THT was 49,000, optimum pH was 6.5~6.8 and optimum temperature was 55° C. Substrate specificity of the purified recombinant potato THT to hydroxycinnamic acid derivatives was investigated. As a result, substrate specificity to feruloyl-CoA was the best and substrate specificities to cinnamoyl-CoA, 4-courmaroyl-CoA and sinapoyl-CoA followed in that order. Substrate specificity of potato THT to amines was also investigated using feruloyl-CoA as a hydroxycinnamic acid derivative substrate. As a result, substrate specificity to tyramine was the greatest, and substrate specificities to octopamine, to dopamine and to noradrenaline were next in order. When coumaroyl-CoA was used as a substrate, substrate specificity of potato THT to tyramine was increased more than 10 times. Other amines such as tryptamine, agmatine, putricine, cadaverin, spermidine and spermine were not used as a substrate. And, THT worked as a competitive inhibitor of those substrates.

Tobacco cell culture solution was treated with pronase, an elicitor to induce THT enzyme activity. Then, tobacco THT was partially purified by chromatography (Negrel et al., Eur. J. Biochem. 247, 1127–1135, 1997). Based on the data of amino acid sequences of the purified enzyme, cDNA clone was obtained by the conventional method (Schmidt et al., J. Biol. Chem. 274, 4273–4280, 1999). 6 histidines were attached onto an amino-terminal of the above tobacco THT gene, which was expressed by *E. coli* expression vector pQ30. The expression of a target protein was induced by IPTG, and then the protein was purified by an affinity purification method, resulting in tobacco THT. The purified tobacco THT showed the best hydroxycinnamic acid derivative substrate specificity to cinnamoyl-CoA and feruloyl-CoA, and showed the best amine substrate specificity to octopamine when feruloyl-CoA was used as a donor.

THT gene was also cloned from a UV-irradiated hot pepper by differential screening technique (Back et al., Plant Cell Physiol. 42, 475–481, 2001). Substrate specificity of hydroxycinnamic acid derivatives of purified recombinant hot pepper THT was greatest to cinnamoyl-CoA and substrate specificities to sinapoyl-CoA, feruloyl-CoA and coumaroyl-CoA followed in that order. The maximum reaction velocity ($V_{max}$) of cinnamoyl-CoA was 15 times higher than coumaroyl-CoA. Substrate specificity of hot pepper THT to amines was greatest to tyramine and next greatest to octopamine. The maximum reaction velocity ($V_{max}$) of tyramine was 1.5 fold higher than octopamine. mRNA of hot pepper THT gene was expressed in every tissue and THT enzyme was over-expressed when a tissue was wounded.

As explained above, plant THT enzyme synthesizes various N-(hydroxycinnamoyl)-amines such as feruloyltyramine, feruloyloctopamine, 4-coumaroyltyramine, feruloyl-3'-methoxyoctopamine, 4-coumaroyloctopamine, by using hydroxycinnamic acid derivatives and amines as a substrate. But, there has been no such report so far that THT enzyme uses serotonin as its amine substrate.

In the meantime, serotonin derivatives such as feruloylserotonin and coumaroylsrotonin, a sort of N-(hydroxycinnamoyl)-amines, are known to be detected only in certain families of plant seeds by a very small amount. According to an earlier report, serotonin derivatives were separated from *Carthamus tinctorius* and had an anti-oxidant activity (Zhang et al., Chemical & Pharma. Bull. 44, 874–876, 1996). After then, an anticancer activity of serotonin derivatives was additionally reported (Kawashima et al., J. Interferon & Cytokine Res. 18, 423–428, 1998). And further, Korean patent No. 10-0354791 discloses a novel use of feruloylserotonin and coumaroylserotonin, an activity to promote bone-formation.

Although the usefulness of the serotonin derivatives was confirmed, a mechamism for biosynthesizing serotonin derivatives and a functional plant producing serotonin derivatives have not been reported yet. In addition, it has not been reported yet that THT enzyme can synthesize serotonin derivatives by using serotonin as an amine substrate.

SUMMARY OF THE INVENTION

In the course of conducting continuous studies on a method for biosynthesizing serotonin derivatives, the present inventors have identified that serotonin derivatives can be biosynthesized in plants by treating plants with inducers for serotonin derivative biosynthesis or by over-expressing THT enzyme in plants, and thus they have completed the present invention.

It is an object of the invention to provide a method for biosynthesizing the serotonin derivatives including a step of treating plants with inducers for serotonin derivative biosynthesis.

It is another object of the invention to provide a method for biosynthesizing the serotonin derivatives including a step of inducing over-expression of tyramine-N-(hydroxycinnamoyl)transferase in plants.

It is another object of the invention to provide a transgenic plant biosynthesizing serotonin derivatives by introducing a foreign gene encoding tyramine-N-(hydroxycinnamoyl) transferase into the plant.

It is another object of the invention to provide plant tissues or seeds derived from the above transgenic plant.

DETAILED DESCRIPTION OF PREFERRED EMBODIMENTS

In order to achieve the above objects, the present invention provides a method for biosynthesizing the serotonin derivatives including a step of treating plants with inducers for serotonin derivative biosynthesis.

The present invention also provides a method for biosynthesizing the serotonin derivatives including a step of inducing over-expression of tyramine-N-(hydroxycinnamoyl) transferase in plants.

The present invention further provides a transgenic plant in which serotonin derivatives are biosynthesized by introduction of a foreign gene encoding tyramine-N-(hydroxycinnamoyl)transferase.

The present invention also provides plant tissues or seeds derived from the above transgenic plant.

Hereinafter, the present invention is described in detail.

It is known that only few plants synthesize serotonin derivatives. But, the present inventors have confirmed first that serotonin derivatives can be biosynthesized in a plant when the plant is treated with aromatic amines or hydroxycinnamic acid compounds. In addition, the present inventors have confirmed first that serotonin derivatives can also be synthesized in a plant when THT enzyme is over-expressed in the plant.

In addition, the present inventors have confirmed that when THT enzyme is over-expressed in a plant, serotonin derivatives can be synthesized in the plant without aromatic amines or hydroxycinnamic acid compounds.

Thus, a method for biosynthesizing serotonin derivatives of the present invention is characterized by treating a plant with inducers for serotonin derivative biosynthesis such as aromatic amines or hydroxycinnamic acid compounds.

The method for biosynthesizing serotonin derivatives of the present invention is also characterized by inducing over-expression of tyramine-N-(hydroxycinnamoyl)transferase in a plant.

The plant for the present invention is not limited to a specific one, but comprises food crops such as rice, wheat, barley, corn, bean, potato, red-bean, oat and Indian millet; vegetables such as hot pepper, Chinese cabbage, radish, strawberry, tomato, watermelon, cucumber, cabbage, melon, pumpkin, Welsh onion, onion and carrot; special crops such as ginseng, tobacco, cotton, sesame, sugar cane, sugar beet, *Perilla japonica*, peanut and rape; fruits such as apple, jujube, peach, kiwifruit, mandarin orange, persimmon, plum, apricot and banana; and feed crops such as ryegrass, red clover, orchardgrass, alfalfa, tall fescue and perennial ryegrass. In a preferred embodiment of the present invention, rice, one of food crops, and hot pepper, one of vegetable crops, were used (see Example 1).

The serotonin derivatives of the present invention mean hydroxycinnamoyl serotonin compounds generated by polymerization of hydroxycinnamic acid derivatives and serotonin. Feruloylserotonin or coumaroylserotonin which has activities of anticancer, anti-oxidation and promoting bone-formation is more preferred.

1. Treating a Plant with Inducers for Serotonin Derivative Biosynthesis

A method for biosynthesizing serotonin derivatives of the present invention includes a step of treating a plant with inducers for serotonin derivative biosynthesis.

The 'inducers for serotonin derivative biosynthesis' of the present invention mean compounds that can induce the generation of serotonin derivatives in a plant by activating synthesis of serotonin derivative and/or its movement after being absorbed in a plant. The inducers for serotonin derivative biosynthesis comprise aromatic amines, hydroxycinnamic acid derivatives or a mixture thereof.

The aromatic amines comprise tyramine, tryptamine, serotonin, dopamine, noradrenaline and octopamine. The hydroxycinnamic acid compounds comprise coumaric acid, caffeic acid, ferulic acid, cinnamic acid and sinapic acid. Besides, as commonly known, chitin, fungal cell wall extracts and jasminic acid (Facchini et al., *Plant Physiol.* 111, 687–697, 1996; Randhir et al., *Process Biochemistry* 37, 1247–1256, 2002; Ishihara et al., *Biosci. Biotech. Biochem.* 66, 2176–2182, 2002) can be included as an inducer for secondary metabolite biosynthesis in a plant.

The inducers for serotonin derivative biosynthesis of the present invention can be either extracted from nature or produced by chemical synthesis or purchased.

The method to treat a plant with inducers for serotonin derivative biosynthesis is preferably to add the inducers to a plant growth medium or to treat soil with the same directly in order for plant roots to absorb the inducers. The mentioned plant growth medium means a composition containing nutrients necessary for the growth of a plant. As for the nutrients, organic nutrients such as carbon source, growth regulation factor, vitamin, amino acid, etc, and in variety of inorganic nutrients can be included. MS medium and modified B5 medium are commonly used, but any plant growth medium that seems to be the most appropriate for each experiment can be selected according to a kind of plant.

When a plant is treated with serotonin, one of inducers for serotonin derivative biosynthesis, it is preferred to treat the serotonin to a leaf and stem or a sarcocarp of a plant using a conventional method known to those skilled in the art.

Therefore, the inducers for serotonin derivative biosynthesis of the present invention can induce biosynthesis of serotonin derivatives in plants by treating the inducers to a plant according to a method selected from a group consisting of (a) adding to a plant growth medium; (b) adding to soil; (c) treating to leaves and stems; and (d) treating to sarcocarps.

The preferred concentration of the inducers for serotonin derivative biosynthesis when added to a plant growth medium may be 10~50 μM, and the concentration of 50 μM may be more preferred.

The inducers for serotonin derivative biosynthesis may be added to soil at the rate of 100,000~300,000 L/ha with concentration of 10~100 μM. A treatment at the rate of 300,000 L/ha with the concentration of 100 μM is more preferred.

However, in the case where serotonin is used as an inducer for serotonin derivative biosynthesis, it is preferably diluted with water to 0.1~1 mM concentration. And the dilution to 1 mM is more preferred. The treatment amount of serotonin is preferably 10,000 L/ha.

There is no fixed time for the treatment of inducers for serotonin derivative biosynthesis. Although any time throughout the growth of a plant is possible, the latter stage of growth is preferred to minimize growth inhibition by the treatment of the above inducers and to accumulate serotonin derivatives in a seed or a sarcocarp of a plant. That is, it is preferred to treat inducers for serotonin derivative biosynthesis to a plant at a specific period such as a sarcocarp-forming stage or a seed-ripening stage, in order to accumulate serotonin derivatives in a seed or a sarcocarp. For example, when rice is treated with inducers for serotonin derivative biosynthesis, 30~40 days after heading is preferred and 40 days after heading is more preferred. When hot pepper is treated with inducers for serotonin derivative biosynthesis, the flowering period is preferred.

In a preferred embodiment of the present invention, the soil where rice (about 40 days after heading) was growing was treated with inducers for serotonin derivative biosynthesis such as amine compounds, for example, tyramine and tryptamine; and hydroxycinnamic acid compounds, for example, cinnamic acid, coumaric acid, caffeic acid and ferulic acid. After cultivating 20~30 days more, the present inventors investigated the content of serotonin derivatives in a seed of rice. As a result, serotonin derivatives were not detected in a seed of rice that was not treated with inducers for serotonin derivative biosynthesis. But, serotonin derivatives such as coumaroylserotonin and feruloylserotonin were detected in a seed of rice that was treated with inducers for serotonin derivative biosynthesis (see Example 1-1).

In another preferred embodiment of the present invention, soil where hot pepper in the flowering period was growing was treated with inducers for serotonin derivative biosynthesis such as amine compounds, for example, tyramine and tryptamine; and hydroxycinnamic acid compounds, for example, cinnamic acid, coumaric acid, caffeic acid and ferulic acid. After cultivating 20 more days, the present inventors investigated the content of serotonin derivatives in sarcocarps of hot pepper. As a result, serotonin derivatives were not detected in sarcocarps of hot pepper that was not treated with inducers for serotonin derivative biosynthesis. However, serotonin derivatives such as coumaroylserotonin and feruloylserotonin were detected in sarcocarps of hot pepper treated with inducers for serotonin derivative biosynthesis (see Example 1-2).

In another preferred embodiment of the present invention, serotonin dissolved in water was sprayed on sarcocarps of hot pepper and serotonin derivatives included in the sarcocarp were investigated after a certain period. As a result, serotonin derivatives were not detected in a control group that was not treated with serotonin. On the contrary, serotonin derivatives were detected a lot in sarcocarps of hot pepper treated with serotonin (see Example 2).

From the above result, the present inventors confirmed that serotonin derivatives could be biosynthesized in plants by treating them with inducers for serotonin derivative biosynthesis.

2. Inducement of Over-Expression of Tyramine N-(hydroxy cinnamoyl)transferase in Plants A method for biosynthesizing serotonin derivatives in plants of the present invention is also characterized by inducing over-expression of THT enzyme therein.

In order to biosynthesize the serotonin derivatives in plants, a sarcocarp of a plant could be wounded or a foreign gene encoding THT enzyme could be introduced into a plant.

Preferably, the method for making a wound in a sarcocarp is to incise a part of the sarcocarp by same size.

In a preferred embodiment of the present invention, fully matured sarcocarps of hot pepper were cut by 0.5 mm and after a certain period, the content of serotonin derivatives included therein was investigated. As a result, serotonin derivatives were not detected in sarcocarps of hot pepper that has not been wounded. But, the serotonin derivative content was great in sarcocarps of hot pepper that has been wounded (see Example 3).

From the above result, it was confirmed that serotonin derivatives could be biosynthesized in plants by making the plants wounded.

In addition, inducement of over-expression of THT enzyme in plants can be accomplished by introducing a recombinant vector including a gene encoding THT enzyme as follows.

For a gene encoding THT in the present invention, a THT gene originated from *Solanum* is preferred, a THT gene originated from *Capsicum annuum* is more preferred and cDNA having a base sequence represented by SEQ. ID. No 3 originated from hot pepper (*Capsicum annuum*) is the most preferred. The target THT gene can be amplified by PCR generally known to those skilled in the art. In an Example of the present invention, a whole cDNA containing hot pepper THT gene (Back et al., *Plant Cell Physiol*. 42, 475–481, 2001) was used as a template for PCR.

A recombinant vector including a gene encoding THT of the present invention can be constructed by using a plant expression vector as a basic vector. And a binary vector, a cointegration vector or another basic vector designed to be expressed in a plant, which dose not include T-DNA region is available as well. There are in variety of binary vectors generally used for the transformation of *Monocotyledoneae*, in particular, a rice plant, and almost every binary vector can be obtained from an international center like CAMBIA (Center for the Application of Molecular Biology to International Agriculture, GPO Box 3200, Canberra ACT2601, Australia) and research centers of universities. A basic binary vector is built by making Ti plasmid to be a main body, on which a transformant selection marker gene, a promoter and a transcription termination region gene, etc, are located in right and left borders with being modified.

A recombinant vector of the present invention is characterized by including a gene encoding THT, a promoter regulating a plant specific expression which is operably linked to said gene and a selection marker gene. The promoter regulating a plant specific expression is selected from a group consisting of maize ubiquitin promoter, cassava mosaic virus promoter, cauliflower mosaic virus 35S promoter (CaMV 35S promoter), actin promoter, PG promoter and endosperm-specific promoter, etc, but not limited thereto and ubiquitin promoter is preferred. In order to promote biosynthesis of serotonin derivatives by inducing over-expression of THT gene in a seed of a plant, a seed specific promoter such as glutein promoter is preferred for a plant specific expression-regulating promoter of the present invention. The selection marker can be one of antibiotics resistant gene, herbicide resistant gene, metabolism related gene, luminous gene, GFP (green fluorescence protein) gene, GUS (β-glucuronidase) gene and GAL gene (β-glucuronidase), etc, but not limited thereto. Particularly, neomycin phosphotransferase II (NPT II) gene, hygromycin phosphotransferase gene, phosphinothricin acethyltransferase gene or dihydrofolate reductase gene is available, and hygromycin transferase gene is preferred. In a preferred embodiment of the present invention, according to a molecular biological method well known to those skilled in the art, *Bacillus subtillis* protox gene was removed from a known binary vector pGA1611:C (Accession No: KCTC 0692BP), into which a full-length hot pepper THT cDNA was inserted instead, resulting in the construction of a binary vector pGA 1611:THT (see FIG. 1).

The introduction of a recombinant vector including a gene encoding THT into a plant can be performed by a conventional transformation method commonly known to those skilled in the art. Plant transformation can be performed by *Agrobacterium*-mediated transformation, using methods examples in literatures (Horsch et al., *Science* 227:1229–1231, 1985). For example, an *Agrobacterium*-mediated transformation method for rice transformation is explained in many literatures (An et al., *EMBO J* 4:227–288, 1985). An *Agrobacterium* used for a host for transformation can be either *Agrobacterium tumefaciens* or *Agrobacterium rhizogenes*. *Monocotyledoneae* can be transformed by PEG or electroporation, precisely, by inserting a foreign gene directly into a protoplast or by taking advantage of particle bombardment into a callus tissue. In addition, a transformation method using a single DNA or a simultaneous transformation method is also available for a plant transformation. In a preferred embodiment of the present invention, the above binary vector pGA1611:THT was inserted into *Agrobacterium tumefaciens* LBA4404 (Cat. NO. 18313-015, GibcoBRL, USA) by freezing-thawing method (An, *Methods Enzymol* 153: 292–305, 1987), with which a callus induced from embryo disc of rice was transfected, resulting in the preparation of a transformant (see Example 4-2).

In a preferred embodiment of the invention, in order to investigate whether THT gene was inserted stably into a genome of transgenic rice, and to quantify the insertion, a genomic DNA of the transgenic rice in $T_0$ generation was extracted, followed by Southern blotting. As a result, every transgenic line, except three of those, had genomic DNAs including hot pepper THT gene (see Example 4-3 and FIG. 2).

In order to confirm the inheritance of hot pepper THT gene inserted in a genome of transgenic rice, transgenic rice in $T_0$ generation having resistance against hygromycin was self-pollinated, producing seeds ($T_1$ generation). The obtained seeds were germinated in a medium containing hygromycin. Then, the hygromycin resistant individual of each transgenic line and sensitive one were investigated and the occurrence ratio thereof was calculated. As a result, the segregation ratio was 3:1, suggesting that hot pepper THT gene inserted in a single locus of genome of rice was segregated and expressed according to Mendel's law (see Example 4-4 and Table 5).

In order to investigate whether mRNA and a target protein were expressed stably from hot pepper THT gene, northern blotting and western blotting were performed with transgenic rice in $T_1$ generation. As a result, mRNA of hot pepper THT gene was over-expressed (see Example 4-5 and FIG. 3A) and hot pepper THT protein was always expressed in transgenic rice plants (see Example 4-6 and FIG. 3B).

In order to investigate whether THT protein expressed in a transgenic plant have an enzyme activity, a protein extract obtained from leaves of the plant was added to a reaction mixture including feruloyl-CoA and tyramine, which have been known as the best THT specific substrates, to measure the production of feruloyltyramine. As a result, the enzyme activity was observed neither in a wild type control(W) nor in a transgenic control(TC), none of them had hot pepper THT gene. On the contrary, the enzyme activity was very high in transgenic rice in which hot pepper THT gene was inserted (see Example 4-7 and FIG. 4).

In an embodiment of the present invention, transgenic rice, in which hot pepper THT enzyme was over-expressed, was raised on the soil without a special treatment, then the content of serotonin derivatives in seeds or leaves and stems of the rice was investigated. As a result, serotonin derivatives were not detected in leaves and stems of rice. But, it was confirmed that serotonin derivatives were biosynthesized in seeds of rice at the rate of 689 ng/1 g seed (see Example 5).

From the results, it was confirmed that serotonin derivatives could be biosynthesized in plants by over-expressing THT enzyme in the plants.

Further, a method for biosynthesizing serotonin derivatives of the present invention can additionally include a step of treating a transgenic plant, in which THT enzyme was over-expressed, with inducers for serotonin derivative biosynthesis.

A method to treat a plant with inducers for serotonin derivative biosynthesis is just as explained above.

In an embodiment of the present invention, tansgenic rice having over-expressed hot pepper THT enzyme was cultured in a medium supplemented with inducers for serotonin derivative biosynthesis such as an amine compound like tyramine or a hydroxycinnamic acid compound like coumaric acid. Then, the content of serotonin derivatives in leaves and stems of rice was investigated. As a result, serotonin derivatives such as feruloylserotonin and coumaroylserotonin were biosynthesized in every transgenic line at the rate of 174 μg at average per 1 g leaves and stems (see Example 6-1 and Table 6).

In another embodiment of the present invention, transgenic rice treated with different inducers for serotonin derivative biosynthesis, for example, tyramine, tryptamine, cinnamic acid, coumaric acid, caffeic acid and ferulic acid, was cultivated. Then, the content of serotonin derivatives in seeds of rice was investigated. As a result, the amount of produced serotonin derivatives in transgenic rice treated with inducers for serotonin derivative biosynthesis was greater than that in a group not treated with the inducers. In particular, the content of serotonin derivatives in transgenic rice was 6~25 times more than that in wild type rice (see Example 6-2 and Table 7).

From the results above, the present inventors confirmed that serotonin derivatives are biosynthesized in a transgenic plant having over-expressed THT gene when treated with inducers for serotonin derivative biosynthesis, and a transgenic plant produced more serotonin derivatives more than a wild type plant.

In an embodiment of the present invention, 1 mM of serotonin as a substrate of THT enzyme was sprayed on leaves of transgenic rice. 24 hours later, the content of serotonin derivatives in the leaves was measured. As a result, 2 μg of feruloylserotonin was detected in leaves and stems of rice treated with serotonin (see Example 6-3).

From the result, it was confirmed that serotonin derivatives can be biosynthesized in plants by treating leaves of a transgenic plant having over-expressed THT gene with serotonin.

The present invention further provides a method for biosynthesizing the serotonin derivatives, which additionally includes a step of separating and purifying the serotonin derivatives from a transgenic plant, prepared by a method of the present invention. Separation and purification of serotonin derivatives are performed by a conventional method for extracting a specific chemical compound from a plant that is well known to those skilled in the art.

For example, a solvent extraction method can be used, which is extracting an effective ingredient by using a solvent after drying and pulverizing a target plant, and chromatography is usefull to purify the obtained extract.

Serotonin derivatives such as feruloylserotonin and coumaroylserotonin, which were biosynthesized by a method of the present invention, can be used after being separated and purified from a transgenic plant following a conventional method. However, it is preferred in terms of cost and process to use either a transgenic plant cell itself, a part of a transgenic plant which is re-differentiated from the plant, a seed or an extract from the same, without separation or purification, if a transgenic plant is edible.

From all the above results, it was concluded that THT enzyme uses serotonin as an amine substrate for biosynthesis of the serotonin derivatives in a plant body (Example 7). And it was identified that THT enzyme does not biosynthesize the tyramine derivatives using tyramine having substrate specificity as a substrate, which seems attributable to the fact that tyramine itself does not exist in a plant or its substrate specificity is inferior to that of serotonin. Even though tyramine was added to a plant culture medium, the tyramine was not used as a substrate. That seems attributable to the fact that added tyramine is decomposed into quinone fast by phenol oxidase in a plant (Negrel et al., *Plant Physiol.* 103, 329–334, 1993).

The present inventors also introduced THT gene into a plant to induce over-expression of THT gene, and confirmed that over-expressed THT enzyme uses serotonin and hydroxycinnamic acid derivatives existing in the plant as substrates for biosynthesis of the serotonin derivatives.

The present inventors further confirmed that serotonin derivative biosynthesis can be accelerated when inducers for serotonin derivative biosynthesis are given to a plant having over-expressed THT gene.

In order to obtain positive evidence for the assumption that hot pepper THT enzyme might use serotonin and hydroxycinnamic acid derivatives as substrates for biosynthesis of the serotonin derivatives, the present inventors induced an enzyme reaction in vitro by mixing a purified recombinant hot pepper THT enzyme, feruloyl-CoA and serotonin together. Then, a reaction product was analyzed by HPLC. As a result, biosynthesis of feruloylserotonin was confirmed (see Example 7 and FIG. 5E). Besides, when coumaroyl-CoA and serotonin were added as a substrate, biosynthesis of coumaroylserotonin by hot pepper THT enzyme was also confirmed (not shown).

As explained above, the present inventors could confirm that hot pepper THT enzyme uses serotonin and hydroxycinnamic acid derivatives as substrates to biosynthesize the serotonin derivatives such as feruloylserotonin and coumaroylserotonin, and such characteristics of THT enzyme is first proved by the present inventors.

The present invention also provides a transgenic plant in which a foreign gene encoding tyramine N-(hydroxycinnamoyl)transferase was inserted and serotonin derivatives were biosynthesized by re-differentiation during tissue culture.

The plant of the present invention includes all of plant organs, plant tissues, plant cells, seeds and calli. The transgenic plant of the present invention includes food crops such as rice, wheat, barley, corn, bean, potato, red-bean, oat and Indian millet; vegetables such as hot pepper, Chinese cabbage, radish, strawberry, tomato, watermelon, cucumber, cabbage, melon, pumpkin, Welsh onion, onion and carrot; special crops such as ginseng, tobacco, cotton, sesame, sugar cane, sugar beet, *Perilla japonica*, peanut and rape; fruits such as apple, jujube, peach, kiwifruit, mandarin orange, persimmon, plum, apricot and banana; and feed crops such as ryegrass, red clover, orchardgrass, alfalfa, tall fescue and perennial ryegrass. Among them, rice is the most preferred as a transgenic plant. In particular, if an edible plant is transformed to induce serotonin derivative biosynthesis by over-expression of THT, eating the plant itself is possible, which brings fast and better anticancer effect, anti-oxidation effect and born-formation promoting effect. By taking advantage of a method for biosynthesizing serotonin derivatives of the present invention, serotonin derivatives can be accumulated in a seed or a sarcocarp of a plant, which can also be eaten as it is.

The trarsgenic plant cells of the present invention can be re-differentiated into the whole plants through the process of callus inducement, rooting and soil acclimation according to a standard technique of the art.

In an embodiment of the present invention, transgenic plant cells, prepared by a method of the present invention, were cultured in a selection medium containing 50 μg/ml of hygromycin, which were then transferred to a re-differentiation medium to induce leaves from live hygromycin-resistant callus, followed by further culture. As a result, 4–8% calli were re-differentiated into shoots. The re-differentiated shoots were transferred to a root-inducing medium and further cultured. At last, authentic plants over-expressing THT were obtained (see Example 4-2).

BRIEF DESCRIPTION OF THE DRAWINGS

The application of the preferred embodiments of the present invention is best understood with reference to the accompanying drawings, wherein.

(Ubi-P: maize ubiquitin promoter, THT: hot pepper tyramine N-(hydroxy cinnamoyl)transferase gene, Tnos: nopaline synthesis terminator gene, $P_{35S}$: cauliflower mosaic virus 35S promoter (CaMV 35S promoter), HPT: hygromycin phosphotransferase, TiA6-7: octopine type TiA6-7 terminator gene)

Figure 2:
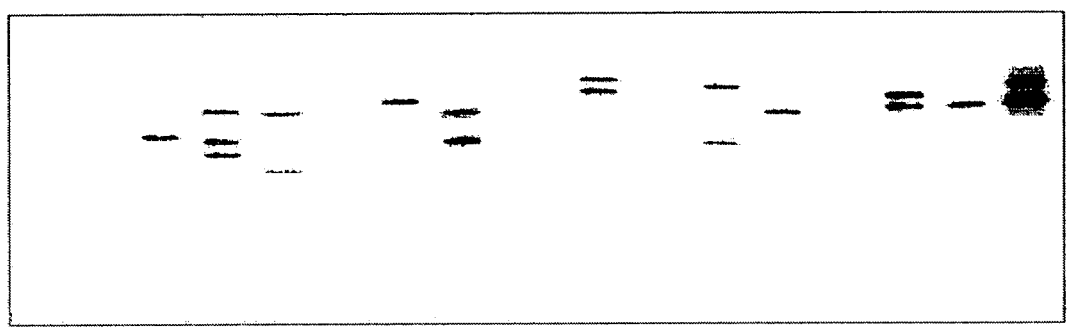

FIG. 2 is a photograph showing the result of southern blotting with transgenic rice in $T_0$ generation.

(W: wild-type control group rice, TC: transgenic control group rice, T8–T23: transgenic rice)

Figure 3:
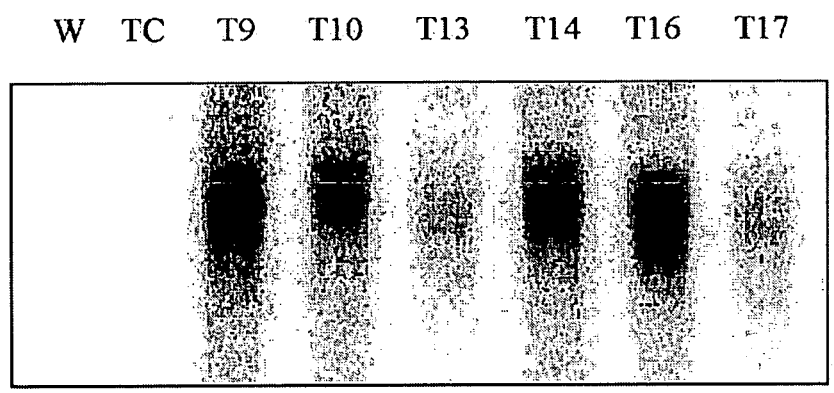
Figure 3:
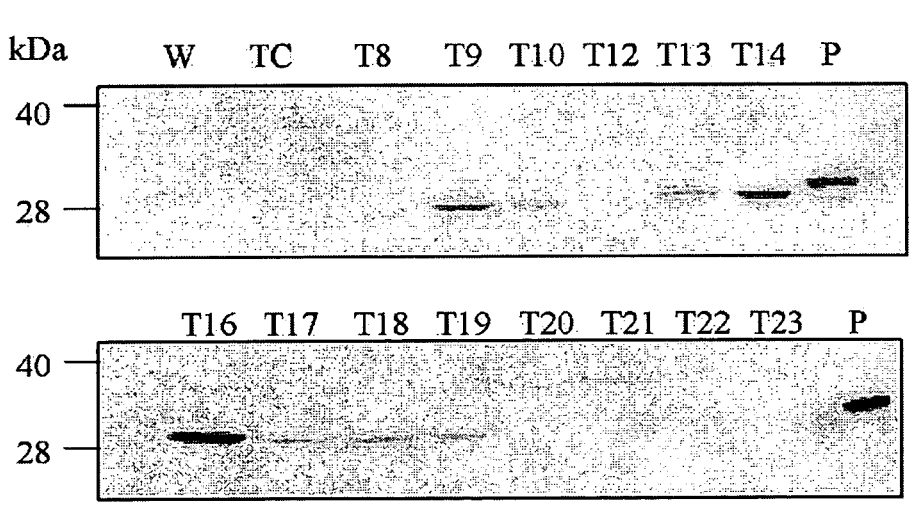

FIG. 3 is a set of photographs showing the result of northern blotting with transgenic rice in $T_1$ generation (A) and the result of western blotting with the same (B).

(W: wild-type control group rice, TC: transgenic control group rice, T8–T23: transgenic rice, P: 20 ng of purified recombinant tyramine N-(hydroxy cinnamoyl)transferase protein)

Figure 4:
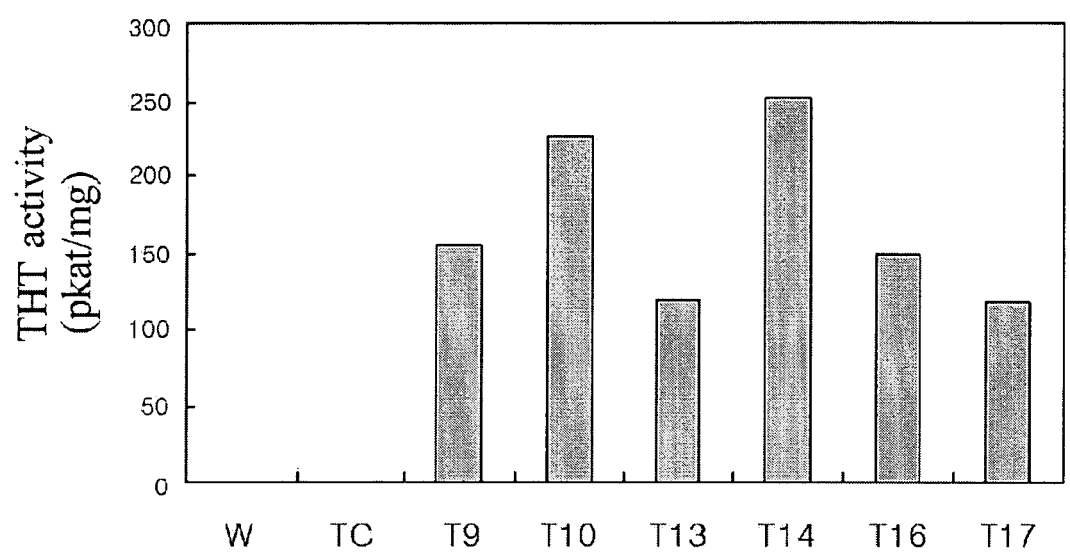

FIG. 4 is a graph showing the enzyme activity of tyramine N-(hydroxy cinnamoyl)transferase included in transgenic rice in $T_2$ generation.

(W: wild-type control group rice, TC: transgenic control group rice, T9–T17: transgenic rice)

Figure 5:
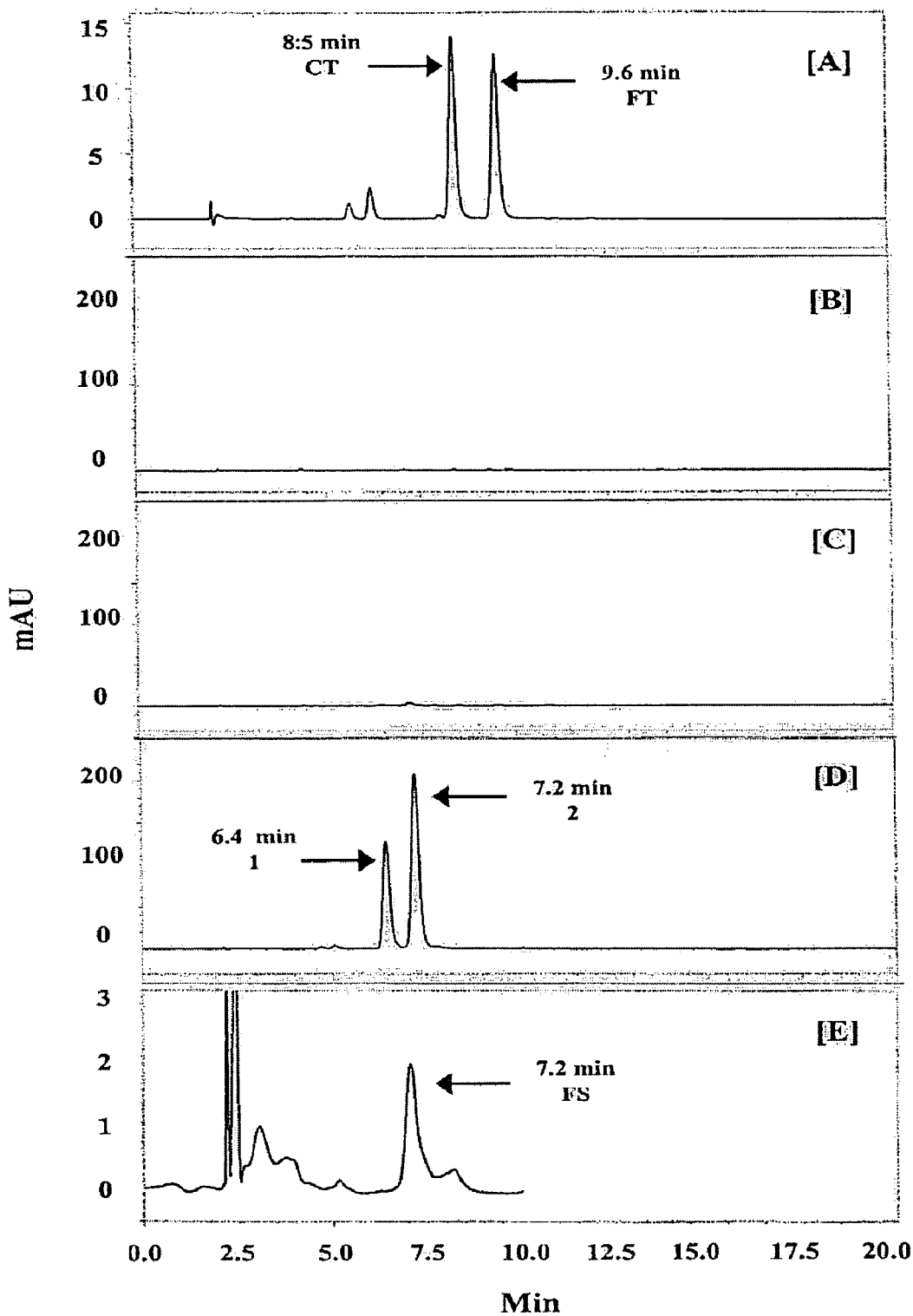

FIG. 5 is HPLC data showing the synthesis of hydroxycinnamoyl amines in transgenic rice in $T_2$ generation.

(A: standard mixture of coumaroyltyramine and feruloyltyramine (CT: coumaroyltyramine, FT: feruloyltyramine); B: wild-type control group rice; C: transgenic rice; D: transgenic rice cultivated in a medium supplemented with tyramine (CS: coumaroylserotonin, FS: feruloylserotonin); E: purified hot pepper tyramine N-(hydroxycinnamoyl) transferase, feruloyl-CoA and serotonin were used as a substrate)

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Biosynthesis of the Serotonin Derivatives by the Treatment of Inducers for Serotonin Derivative Biosynthesis in Plants <1-1> Biosynthesis of the Serotonin Derivatives by the Treatment of Inducers for Serotonin Derivative Biosynthesis in Rice Rice plants (Variety: Nakdong) having been cultivated in the rice field were treated with inducers for serotonin derivative biosynthesis and then biosynthesis of the serotonin derivatives was investigated.

Inducers for serotonin derivative biosynthesis were prepared by dissolving tyramine, tryptamine, cinnamic acid, coumaric acid, caffeic acid and ferulic acid (Sigma-Aldrich, Korea) in water respectively to make each concentration 100 μM. And then the soil where rice plants (about 40 days after heading) had been growing was treated once with each inducer for serotonin derivative biosynthesis at the rate of 300,000 L/ha, followed by further cultivation for 20 days.

As a control group, rice plant which had been cultivated under the same conditions except the treatment with inducers for serotonin derivative biosynthesis was used.

After harvesting rice, seeds of the rice were peeled to obtain brown rice. N-(hydroxycinnamoyl)-amines were extracted from 1 g of the brown rice by known method (Ishihara et al., *Biosci. Biotechnol. Biochem.* 64, 1025–1031, 2000), and then, HPLC was performed.

As a result, two compounds having 6.4 minute retention time (compound a) and 7.2 minute retention time (compound b) were confirmed from the extract of rice treated with inducers for serotonin derivative biosynthesis. Ion-spray LC/MS was used to investigate the two compounds. As a result, compound a had 322 molecular weight and a spectrum of m/z(the ratio of mass to charge) 147 to be assumed to have an amide of coumaric acid. And, compound b had 352 molecular weight and a spectrum of m/z 177 to be assumed to have feruloyl. Thus, the two compounds were assumed to be N-(hydroxycinnamoyl)-amines having two nitrogen atoms (data not shown). The compounds a and b were compared with artificially synthesized coumaroylserotonin and feruloylserotonin in mass (MS) and ultraviolet (UV) spectrum. As a result, the compound a was confirmed to be coumaroylserotonin and the compound b was confirmed to be feruloylserotonin. The MS and UV spectrum results of the compounds a and b are represented hereinafter.

Compound a. UV $\lambda_{max}$ (relative intensity): 293 (100), 310 (99) ion-spray MS, m/z (relative intensity): 147 (100, [M-C10H11N2O]+), 323 (25, [M+H]+).

Compound b. UV $\lambda_{max}$ (relative intensity): 294 (89), 316 (100) ion-spray MS, m/z (relative intensity): 177 (100, [M-C10H11N2O]+), 353 (34, [M+H]+).

Coumaroylserotonin and feruloylserotonin included in the extract of seeds of rice, treated with inducers for serotonin derivative biosynthesis, were quantified by HPLC using a standard substance synthesized by a well-known method (Villegas & Brodelius, *Physiol. Plant.* 78, 414–420, 1990).

As a result, the serotonin derivatives were produced most by the treatment of cinnamic acid, second most by the treatment of tyramine and third most by the treatment of ferulic acid. On the contrary, serotonin derivatives such as coumaroylserotonin and feruloylserotonin were not detected in control group rice that had not been treated with inducers for serotonon derivative biosynthesis (Table 1).

TABLE 1

Content of serotonin derivatives in seeds of rice according to the treatment of inducers for serotonin derivative biosynthesis

| Inducers for serotonin derivative biosynthesis | Content of serotonin derivatives (ng/1 g seed) | | |
|---|---|---|---|
| | Coumaroyl Serotonin | Feruloyl serotonin | Total content |
| Not treated (control) | — | — | — |
| Tyramine | 19 | 54 | 73 |
| Tryptamine | 20 | 28 | 48 |
| Cinnamic acid | 48 | 76 | 124 |
| Coumaric acid | 15 | 21 | 36 |
| Caffeic acid | 20 | 23 | 43 |
| Ferulic acid | 33 | 37 | 70 |

<1-2> Biosynthesis of the Serotonin Derivatives by the Treatment of Inducers for Serotonin Derivative Biosynthesis in Hot Pepper Hot pepper (Variety: Pungcheon) was treated with inducers for serotonin derivative biosynthesis, followed by an examination of biosynthesis of serotonin derivatives.

Particularly, inducers for serotonin derivative biosynthesis were prepared by dissolving tyramine, tryptamine, cinnamic acid, coumaric acid, caffeic acid and ferulic acid in water respectively to make each concentration 100 μM. And then the soil where rice plants (about 40 days after heading) had been growing was treated once with each inducer for serotonin derivative biosynthesis at the rate of 300,000 L/ha, followed by further cultivation for 20 days.

The ripe sarcocarps of hot peppers were obtained to investigate the content of serotonin derivatives by the same method as used in the above Example <1-1>. Control group hot pepper was cultivated under the same condition as the experimental group hot pepper except the treatment with inducers for serotonin derivative biosynthesis.

As a result, serotonin derivatives were produced most by the treatment of cinnamic acid, second most by the treatment of ferulic acid and third most by the treatment of tyramine. On the contrary, serotonin derivatives were not detected in sarcocarps of a control group hot pepper not treated with inducers for serotonin derivative biosynthesis.

From the results above, it was confirmed that serotonin derivatives are produced in plants by the treatment of inducers for serotonin derivative biosynthesis (Table 2).

TABLE 2

Content of serotonin derivatives in sarcocarps of hot pepper according to the treatment of inducers for serotonin derivative biosynthesis

| Inducers for serotonin derivative biosynthesis | Content of serotonin derivatives (ng/1 g sarcocarps) | | |
|---|---|---|---|
| | Coumaroyl Serotonin | Feruloyl serotonin | Total content |
| Not treated (control) | — | — | — |
| Tyramine | 150 | 210 | 360 |
| Tryptamine | 61 | 79 | 140 |
| Cinnamic acid | 214 | 276 | 490 |
| Coumaric acid | 120 | 170 | 290 |
| Caffeic acid | 138 | 162 | 300 |
| Ferulic acid | 145 | 230 | 375 |

Example 2

Biosynthesis of the Serotonin Derivatives by the Treatment of Serotonin in Hot Pepper Hot pepper (Variety: Pungcheon) was treated with serotonin to investigate biosynthesis of serotonin derivatives.

Serotonin solution (prepared by dissolving serotonin in water to make 1 mM concentration) was sprayed on sarcocarps of hot pepper at the rate of 10,000 L/ha. 72 hours after spraying, sarcocarps were taken to investigate the content of serotonin derivatives, for which the same method in the Example 1 was used. Sarcocarps of hot pepper not treated with serotonin were used as a control.

As a result, a large amount of serotonin derivatives was detected in sarcocarps of hot pepper treated with serotonin. On the contrary, serotonin derivatives were not detected in sarcocarps of a control group hot pepper that had not been treated with serotonin (Table 3).

From the above results, it was confirmed that serotonin derivatives can be biosynthesized in plants by the treatment of serotonin.

TABLE 3

Content of serotonin derivatives in sarcocarps of hot pepper according to the treatment of serotonin

| | Content of serotonin derivatives (ng/1 g sarcocarps) | | |
|---|---|---|---|
| | Coumaroyl Serotonin | Feruloyl serotonin | Total content |
| Not treated (control) | — | — | — |
| Serotonin | 1538 | 1028 | 2566 |

Example 3

Biosynthesis of the Serotonin Derivatives in Wounded Hot Pepper

Sarcocarps of fully ripe hot pepper (Pungcheon), 30 days after flowering, were wounded by 0.5 mm cut. 72 hours later, the content of serotonin derivatives in the hot pepper sarcocarps was investigated by the same method as used in the Example 1. As a control group, sarcocarps of hot pepper not wounded were used.

As a result, a large amount of serotonin derivatives was detected in sarcocarps of wounded hot pepper (Table 4). On the contrary, serotonin derivatives were not detected in sarcocarps of a control group hot pepper not wounded (Table 4).

TABLE 4

Content of serotonin derivatives in sarcocarps of wounded hot pepper

| | Content of serotonin derivatives (ng/1 g sarcocarps) | | |
|---|---|---|---|
| | Coumaroyl Serotonin | Feruloyl serotonin | Total content |
| Not treated (control) | — | — | — |
| Wounding | 500 | 291 | 791 |

Example 4

Preparation of a Transgenic Plant Over-Expressing Hot Pepper THT Gene

<4-1> Cloning of Hot Pepper THT Gene and Construction of an Expression Vector for Transformation PCR (polymerase chain reaction) was performed to amplify hot pepper (*Capsicum annuum*) THT gene. At that time, a fill length cDNA (SEQ. ID. No 3) (Back et al., *Plant Cell Physiol.* 42, 475–481, 2001) of hot pepper THT gene was used as a template, and a forward primer 5'-(atc aagcttatggcttctgctcctcaa)-3' (SEQ. ID. No 1) having HindIII restriction enzyme site (underlined) and a backward primer 5'-(gtggagctcctaacagcttcctgcacc)-3' (SEQ. ID. No 2) having SacI restriction enzyme site (underlined) were used. The PCR product was digested with HindIII and SacI, followed by gel-purification. The purified product was inserted into the same restriction enzyme site of pBluescript (Strategene, USA). Then, the inserted base sequence was examined to check any abnormality.

Figure 1:
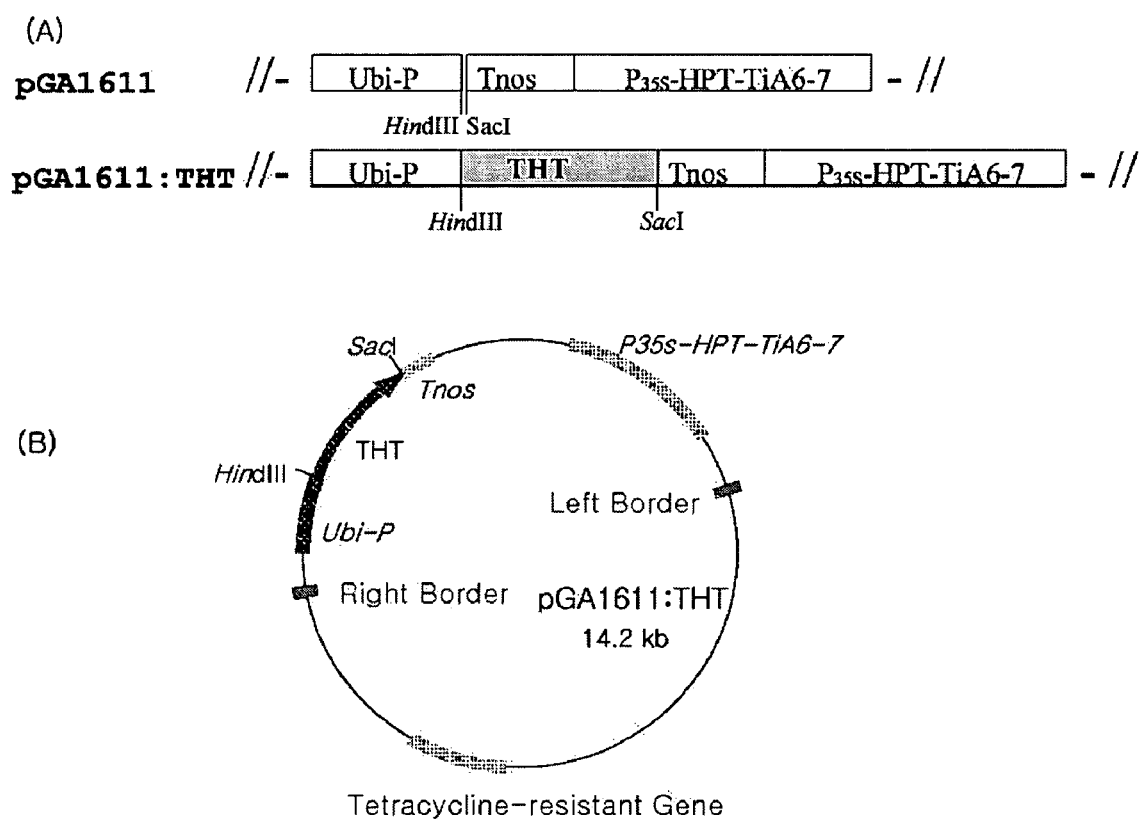
FIG. 1 is a set of schematic diagrams showing the T-DNA regions of binary vectors, pGA1611 and pGA1611:THT (A), and the whole vector pGA1611:THT (B).

In order to construct a vector containing hot pepper originated THT gene, binary vector pGA1611:C (Accession No: KCTC 0692BP) including *Bacillus subtilis* protox gene, constructed in Korean patent NO. 10-0350929 to the present inventors, was used. The *Bacillus subtilis* protox gene included in the binary vector pGA1611:C (Accession No: KCTC 0692BP) was digested with SacI and HindIII. The PCR product prepared above was digested with HindIII and SacI, followed by gel-purification. Then, the purified product was inserted into the digested region of the vector by using ligase to construct binary vector pGA1611:THT expressing a full-length hot pepper THT gene. The structure of the binary vector pGA1611:THT was represented in FIG. 1. As shown in FIG. 1, the binary vector pGA1611:THT constructed in the present Example includes a hot pepper THT gene, a constitutive ubiquitin promoter operably linked to upstream of the hot pepper THT gene and hygromycin phosphotransferase, a selection marker.

<4-2> Transformation and Re-Differentiation of Rice

Binary vector pGA1611:THT constructed in the above Example <4-1> was introduced into an *Agrobacterium tumefaciens* LBA4404 (Cat. No. 18313-015, GibcoBRL, USA). Transformed *Agrobacterium tumefaciens* LBA4404 strain was cultured in YEP medium (1% Bacto-peptone, 1% Bacto-yeast extract and 0.5% NaCl) containing 5 μg/ml of tetracycline and 40 μg/ml of hygromycin at 28° C. for overnight. The culture solution was centrifuged and the obtained pellets were suspended in AA medium (Hiei et al., *Plant Mol. Biol.* 35, 205–218, 1997) containing 100 μg/ml of acetosyringon, thereby preparing transformed *Agrobacterium tumefaciens* LBA4404 suspension. Rice calli were induced from embryo discs of rice (Nakdong) seeded in N6 medium (Rashid et al., *Plant Cell Rep.* 15; 727–730, 1996; Hiei et al., *Plant Mol. Biol.* 35, 205–218, 1997). 3–4 week old calli were deposited in the bacteria suspension for 3 minutes. The suspension was contacted with sterilized filter paper to eliminate excessive bacteria by adsorbing and drying. The co-cultured calli were washed with sterilized water containing 250 μg/ml of Cefotaxim to eliminate remaining bacteria, then transferred to a selection medium containing 50 μg/ml of hygromycin for further culture. As a result, 10–15% calli survived. The survived hygromycin-resistant calli were transferred to a MS medium (containing 2 mg/l benzylaminopurine, 1 mg/l naphthalene acetic acid and 50 mg/l hygromycin), a regeneration medium, and cultured at 28° C. for 3 weeks, in order to induce leaves. 4–8% out of the selected calli above was re-differentiated to shoots. Then, the shoots were transplanted into a root-inducing medium to obtain whole plants (Lee et al., *Plant Cell Physiol.* 41, 743–749, 2000).

In the meantime, transgenic control rice was prepared by transfecting rice plant with pGA1611 vector without hot pepper THT gene, and other preparation procedures for a control were the same as for an experimental group.

<4-3> Southern Blot Analysis with $T_0$ Generation for the Confirmation of THT Gene Insertion In order to investigate whether hot pepper THT gene was stably inserted into a genome of each re-differentiated transgenic rice plant tansgenic line in hygromycin selection medium and to quantify the insertion, genomic DNAs extracted from leaves of 14 transgenic $T_0$ rice plant trarsgenic lines (T8, T9, T10, T12, T13, T14, T16, T17, T18, T19, T20, T21, T22 and T23), a wild type control rice plant and a transgenic control lice plant were digested with HindIII, respectively. Electrophoresis was performed on 0.8% (w/v) agarose gel, resulting in fractionation size by size. After blotting the fractions on nylon membrane (Nylon 66 plus, Pharmacia Biotech.), hybridization was performed with $^{32}$p-labeled hot pepper THT gene.

Since HindIII site was not found in trans-gene treated with a probe, the number of hybridized band was equal to that of inserted transgene in a transgenic plant genome. The result is shown in FIG. 2. Hybridized bands were not detected in genomic DNAs extracted from a wild type control rice plant and a transgenic control rice plant. Among T8–T23 transgenic lines, at least 5 kb long hybridized bands were observed in genomic DNAs of every transgenic line except T12 and T20 transgenic lines, and a faint band was confirmed in T17 transgenic line, which was not well presented in FIG. 2, though. The results suggested that hot pepper THT gene was successfully inserted into genomes of all the transgenic rice plant except T12 and T20 transgenic lines.

<4-4> Separation of Hygromycin-Resistant Rice

In order to confirm whether transgene was stably transmitted from transgenic $T_0$ rice to $T_1$ rice, transgenic rice securing a number of seeds from self-pollinated rice seeds was selected, and $T_1$ generation thereof was investigated. Particularly, 6 $T_0$ transgenic rice lines (T9, T10, T13, T14, T16 and T17) were self-pollinated, resulting in the preparation of seeds ($T_1$ generation). The brown rice was germinated in half concentration of MS solid medium containing 50 μg/ml of hygromycin, during which occurrence ratio of hygromycin-resistant and sensitive ones was investigated. The separation pattern of hygromycin-resistance in the transgenic lines examined above was shown in the below Table 5.

As a result, segregation ratio of hygromycin resistance to sensitivity in every transgenic line except T9 was about 3:1. The result means that transgene inserted in a genome of rice is segregated and expressed as a single dominant gene according to Mendel's law. 2 bands were observed by southern blotting in T10 transgenic line, implying the segregation ratio of 15:1 or 3:1, but the actual segregation ratio was proved to be about 1.5:1, which was close to the segregation ratio of 3:1, so that gene locus was marked as 1. In the meantime, the segregation ratio of hygromycin resistance in T9 transgenic line was 15:1, suggesting that 2 THT genes were located on different sites of the rice plant genome.

TABLE 5

Separation of hygromycin-resistant rice

| transgenic line No. | Number of inserted gene in $T_0$ (Southern blot) | Hygromycin resistance of $T_1$ seeds | | Gene locus |
|---|---|---|---|---|
| | | Number of resistant seeds | Number of sensitive seeds | |
| T9 | 3 | 132 | 7 | 2 |
| T10 | 2 | 79 | 51 | 1 |
| T13 | 1 | 101 | 34 | 1 |
| T14 | 2 | 104 | 33 | 1 |
| T16 | 2 | 99 | 30 | 1 |
| T17 | 1 | 103 | 31 | 1 |

<4-5> Northern Blot Analysis with $T_1$ Generation

In order to investigate whether mRNA of hot pepper THT gene was expressed in $T_1$ generation, northern blotting was performed. $T_1$ generations confirmed to have hygromycin resistance from T9–T17 of the Example <4-4>, wild type control rice plants and transgenic control rice plants were cultured in a green house respectively. A total RNA of the transgenic line, extracted from leaves of the cultured rice plant by using TRI reagent (Sigma Co.), was fractionated on 1% agarose gel containing formaldehyde by using 20 mM Mops [3-(N-morpholino)-propanesulfonic acid] solution as a running buffer. Upon completing fractionation, the gel was blotted on nylon membrane, followed by hybridization with a full-length hot pepper THT. And the result was represented in FIG. 3A.

The mRNA of hot pepper THT gene was expressed neither in wild type control rice (W) nor in transgenic control rice (TC). On the other hand, mRNA of hot pepper THT gene was over-expressed in transgenic lines. In particular, the expressions in T9, T10, T14 and T16 transgenic lines were the highest. From the results, it was confirmed that mRNA of hot pepper THT gene was successfully over-expressed in those transgenic lines.

<4-6> Western Bolt Analysis with $T_1$ Generation

In order to confirm whether hot pepper THT gene inserted in a genome of a T1 generation of a transgenic rice plant was expressed stably to a protein, Western blot analysis was performed with 14 transgenic rice plants (T8, T9, T10, T12, T13, T14, T16, T17, T18, T19, T20, T21, T22 and T23), wild type control rice plants and transgenic control rice plants, for which 20 ng of recombinant THT protein was used as a control. 0.2 g of rice plant leaves was extracted by 1 ml extraction buffer, followed by centrifugation at 14,500 rpm for 10 minutes. 50 μg of the supernatant was separated by electrophoresis (SDS-PAGE), followed by blotting on nitrocellulose membrane. Immune response was induced using THT antibody (Back et al., *Plant Cell Physiol.* 42, 475–481, 2001). Western blotting kit (Boehringer Manheim, Germany) was used to detect bands. The results were shown in FIG. 3B.

A target protein was detected neither in a wild type control rice plant (W) nor in a transgenic control rice plant (TC), since there was no insertion of hot pepper THT gene and the expression of mRNA was not observed thereby either. Among transgenic rice plants prepared in the embodiment of the present invention, just 8 transgenic lines (T9, T10, T13, T14, T16, T17, T18 and T19) expressed hot pepper THT protein. As expected, two tansgenic lines (T12 and T20) without THT gene did not express the protein. In the meantime, some transgenic lines (T8, T21, T22 and T23) that were previously confirmed by Southern blot analysis to have THT gene inserted did not express THT protein, though.

<4-7> Measurement of THT Enzyme Activity in $T_2$ Generation

In the above Example, the expression of THT protein in $T_1$ generation of a transgenic rice plant was confirmed by Western blot analysis. Additionally, in order to investigate whether the protein was expressed stably in $T_2$ generation and had a normal enzyme activity, an enzyme activity of THT protein was measured using feruloyl-CoA and tyramine, THT enzyme substrates. Among $T_1$ generation seeds obtained by self-pollination of 6 transgenic rice plant transgenic lines (T9, T10, T13, T14, T16 and T17), the ones that were confirmed by the method in the above Example <4-4> to have hygromycin-resistance were self-pollinated, resulting in the preparation of $T_2$ generation seeds. A protein extracted from the $T_2$ generation rice plant was added to a reaction mixture containing feruloyl-CoA and tyramine, THT enzyme substrates, then the amount of feruloyl-tyramine, a THT enzyme product, was measured by HPLC. The activity of THT enzyme was measured by calculating the width of peaks obtained form HPLC in terms of pkat (pico katal) unit, and the results were shown in FIG. 4. The THT enzyme activity was detected neither in wild type control rice plants nor in transgenic control rice plants. On the contrary, although there was a little difference in an enzyme activity among plants, the THT enzyme activity was detected in $T_2$ generation rice plants transformed with THT gene. From the results, it was confirmed that THT gene was stably expressed in transgenic rice plants, having a normal enzyme activity.

Example 5

Biosynthesis of Serotonin Derivatives in Transgenic Rice Plants Over-Expressing THT Gene <5-1 > Biosynthesis of Serotonin Derivatives in Leaves and Stems of Transgenic Rice Plants Cultivated in a General Medium HPLC was performed to investigate whether serotonin derivatives were biosynthesized in leaves and stems of $T_2$ generations of transgenic rice plants cultivated in MS solid medium (Duchefa Biochemie, Netherlands). Particularly, 0.3 g of leaves of $T_2$ generation of transgenic rice plants generated from T14 transgenic line and wild type control rice plants, which had been cultivated in MS solid medium (Duchefa Biochemie, Netherlands) were obtained, respectively, and from which hydroxycinnamoyl amines were extracted from them by the same method used in the above Example <1-1>, followed by HPLC.

The results were shown in FIG. 5B and 5C. Neither serotonin derivatives nor hydroxycinnamoyl amines such as tyramine derivatives were found in both $T_2$ generations of transgenic rice plants and wild type control rice plants.

<5-2> Biosynthesis of Serotonin Derivatives in Seeds of Transgenic Rice Plants Cultivated in Rice Field $T_2$ generation seeds of transgenic rice plants were sowed and cultivated for 20 days. Then, the rice plants were transplanted in the rice field at 30 cm×15 cm planting density. HPLC was performed to investigate whether serotonin derivatives were biosynthesized in $T_2$ generation seeds of the transgenic rice plants cultivated in rice field.

As a result, seeds of transgenic rice plants raised in rice field not treated with inducers for serotonin derivative biosynthesis included a large amount of serotonin derivatives. Precisely, 276 ng of coumaroylserotonin and 413 ng of feruloylserotonin were included in 1 g of seeds, meaning the total content of serotonin derivatives was 689 ng (see Table 7). So, transforming a plant to over-express THT gene itself was good enough to induce serotonin derivative biosynthesis in seeds of plants, without treatment of inducers for serotonin derivative biosynthesis.

Example 6

Biosynthesis of Serotonin Derivatives by the Treatment of Inducers for Serotonin Derivative Biosynthesis in Transgenic Rice Plants Over-Expressing THT Gene <6-1> Content of Serotonin Derivatives Produced in Leaves and Stems of Transgenic Rice Plants Cultivated in a Medium Supplemented with Tyramine or Coumaric Acid It was investigated whether serotonin derivatives was biosynthesized in transgenic rice plants over-expressing THT when cultivated in a medium supplemented with serotonin inducers, tyramine or coumaric acid. $T_2$ generations of the transgenic rice seeds were sown on MS medium (Duchefa Biochemie, Netherlands) supplemented with 50 μM of tyramine or coumaric acid, substrates of hot pepper THT enzyme, which were then further cultured in a sterilized condition with 12 hour light and 12 hour dark cycle. 2 weeks later, hydroxycinnamoyl amines were extracted from leaves of $T_2$ generations of transgenic rice plants and wild type control rice plants, respectively, according to the same procedure as used in the above Example <1-1>, then, HPLC was performed for analysis.

As a result, neither coumaroyltyramine nor feruloyl-tyramine, having 8.5 minute retention time (CT) and 9.6 minute retention time (FT), respectively, was detected in the extract of transgenic rice plants raised in a medium supplemented with tyramine or coumaric acid. However, coumaroylserotonin and feruloylserotonin, having 6.4 minute retention time and 7.2 minute retention time, respectively, were detected in the extract.

From the result, it was confirmed that hydroxycinnamoyl amines such as feruloylserotonin and coumaroylserotonin, were biosynthesized in transgenic rice plants when a growth medium was supplemented with tyramine or coumaric acid. The result of cultivation of transgenic rice plants in a serotonin derivatives medium containing 50 μM of tyramine was represented in Table 6. In conclusion, although the content varied from transgenic lines, serotonin derivatives were biosynthesized in every transgenic line, and the average content of biosynthesized serotonin derivatives was 174 µg per 1 g of leaves and stems. In the mean time, a small amount of serotonin derivatives was detected in a control, which was 1 µg/1 g of leaves and stems.

TABLE 6

Content of serotonin derivatives produced in leaves and stems of transgenic rice plants cultivated in a medium supplemented with tyramine

| | | Coumaroyl serotonin (µg/g leaves and stems) | Feruloyl serotonin (µg/g leaves and stems) | Total content of serotonin derivatives |
|---|---|---|---|---|
| Wild-type control (W) | | 0 | 1 | 1 |
| Transgenic control (TC) | | 0 | 1 | 1 |
| Transgenic rice | T9 | 24 | 24 | 48 |
| | T10 | 86 | 114 | 200 |
| | T13 | 224 | 200 | 424 |
| | T14 | 46 | 78 | 124 |
| | T16 | 50 | 70 | 120 |
| | T17 | 36 | 92 | 128 |
| | Mean | 78 | 96 | 174 |

<6-2> Comparison of Serotonin Derivative Contents Produced in Seeds of Transgenic Rice Plants According to the Treatment of Various Inducers for Serotonin Derivative Biosynthesis Among $T_2$ generations of transgenic rice plants, T14 was transplanted in the soil, to which inducers for serotonin derivative biosynthesis were treated. After cultivation, the contents of serotonin derivatives in seeds of the transgenic rice plants were investigated.

As inducers for serotonin derivative biosynthesis, tyramine, tryptamine, cinnamic acid, coumaric acid, caffeic acid and ferulic acid were used. Precisely, the inducers for serotonin derivative biosynthesis were dissolved in water, making each concentration 100 µM. Then, the solutions were added at the rate of 300,000 L/ha, to the soil where rice plants (about 40 days after heading) were growing. The plants were cultivated for 20 more days.

The seeds of the plants cultivated above were collected, and the content of serotonin derivatives in them was investigated with the same method as used in the Example <1-1>, which was compared with that in seeds of wild type control rice plants.

As a result, the content of serotonin derivatives in seeds of transgenic rice plants increased when inducers for serotonin derivative biosynthesis had been treated. In particular, the content of serotonin derivatives in seeds of the plants cultivated in a medium supplemented with tyramine was the highest (Table 7).

TABLE 7

Content of serotonin derivatives in seeds of transgenic rice plants cultivated in a medium supplemented with inducers for serotonin derivative biosynthesis

| | Content of serotonin derivative (ng/g seeds) | | |
|---|---|---|---|
| Inducers for serotonin derivative biosynthesis | Coumaroyl serotonin | Feruloyl serotonin | Total content |
| Not treated | 276 | 413 | 689 |
| Tyramine | 314 | 684 | 998 |
| Tryptamine | 376 | 382 | 758 |
| Cinnamic acid | 403 | 406 | 809 |

TABLE 7-continued

Content of serotonin derivatives in seeds of transgenic rice plants cultivated in a medium supplemented with inducers for serotonin derivative biosynthesis

| | Content of serotonin derivative (ng/g seeds) | | |
|---|---|---|---|
| Inducers for serotonin derivative biosynthesis | Coumaroyl serotonin | Feruloyl serotonin | Total content |
| Coumaric acid | 325 | 599 | 924 |
| Caffeic acid | 368 | 430 | 798 |
| Ferulic acid | 313 | 537 | 850 |

The content of serotonin derivatives in seeds of transgenic rice plants above was compared with that in seeds of wild type rice plants of Example <1-1>. As a result, serotonin derivatives were generated in seeds of transgenic rice plants 6~25 fold more than in seeds of wild type rice plants.

<6-3> Comparison of Serotonin Derivative Contents in Leaves and Stems of Transgenic Rice Plants According to the Treatment of Serotonin Among $T_2$ generations of transgenic rice plants, T14 was transplanted in the soil, and serotonin was sprayed on leaves and stems. After cultivating for a while, the content of serotonin derivatives in leaves and stems of the transgenic rice plants was investigated.

Particularly, serotonin was dissolved in water, making the concentration 1 mM. The solution was sprayed on leaves and stems of T14 (about 40 days after seeding), at the rate of 300,000 L/ha, which were cultivated for 1 more days. The leaves and stems of the plants cultivated above were collected, and the content of serotonin derivatives in them was investigated by the same method as used in the Example <1-1>.

As a result, feruloylserotonin was detected in leaves and stems of the transgenic rice plants treated with serotonin at the rate of about 2 µg per 1 g of leaves and stems.

Example 7

Investigating Whether Serotonin is Used as a Substrate of Hot Pepper THT Enzyme

In order to confirm whether hot pepper THT enzyme could use serotonin as an amine substrate, hot pepper THT protein, in which 6 histidines were attached on carboxy-terminal, was purified by affinity chromatography (Back et al., *Plant Cell Physiol.* 42, 475–481, 2001) and used for the experiment. Particularly, 1 µg of the purified hot pepper THT enzyme, 1 mM of feruloyl-CoA (Sigma-Aldrich, Korea) and 10 mM of serotonin (Sigma-Aldrich, Korea) were mixed together, followed by an enzyme reaction at 30° C. for 10 minutes. Upon completing the reaction, the reaction product was analyzed by HPLC.

As a result, the reaction product was identical to feruloylserotonin having 7.2 minute retention time (FIG. 5E). The result suggested that hot pepper THT enzyme uses serotonin as an amine substrate to synthesize feruloylserotonin. In addition, hot pepper THT enzyme synthesized coumaroylserotonin when coumaroyl-CoA and serotonin were provided as substrates (not shown).

INDUSTRIAL APPLICABILITY

As explained hereinbefore, a method of the present invention facilitates biosynthesis of serotonin derivatives such as feruloylserotonin and coumaroylserotonin having activities of anticancer, anti-oxidation and promoting bone-formation. The serotonin derivatives synthesized by the method of the present invention can be either used after being purified or eaten as edible plants themselves.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention of the appended claims.

The invention claimed is:

1. A method for biosynthesizing coumaroylserotonin and/or feruloylserotonin, the method comprising inducing over-expression of tyramine N-(hydroxycinnamoyl)transferase in a plant and purifying coumaroylserotonin and/or feruloylserotonin from tissues and or seeds of the plant, wherein the tyramine N-(hydroxycinnamoyl)transferase is derived from hot pepper.

2. The method derivatives of claim 1, wherein the over-expression of tyramine N-(hydroxycinnamoyl)transferase is induced by wounding sarcocarps of plants.

3. The method of claim 1, wherein the over-expression of tyramine N-(hydroxycinnamoyl)transferase is induced by introducing a gene encoding tyramine N-(hydroxycinnamoyl)transferase into the plant, wherein the gene is derived from hot pepper.

4. The method of claim 3, wherein the gene encoding tyramine N-(hydroxycinnamoyl)transferase is a cDNA comprising SEQ ID NO:3.

5. The method of claim 1, further including a step of feeding inducers for serotonin derivative biosynthesis to the plant over-expressing tyramine N-(hydroxycinnamoyl)transferase.

6. A transgenic plant biosynthesizing coumaroylserotonin and/or feruloylserotonin comprising an introduced gene encoding tyramine N-(hydroxycinnamoyl)transferase, wherein the gene is derived from hot pepper.

7. The transgenic plant of claim 6, wherein the plant is selected from the group consisting of rice, wheat, barley, corn, bean, potato, red-bean, oat, Indian millet, hot pepper, Chinese cabbage, radish, strawberry, tomato, watermelon, cucumber, cabbage, melon, pumpkin, Welsh onion, onion, carrot, ginseng, tobacco, cotton, sesame, sugar cane, sugar beet, *Perilla japonica*, peanut, rape, apple, jujube, peach, kiwifruit, mandarin orange, persimmon, plum, apricot, banana, ryegrass, red clover, orchardgrass, alfalfa, tall fescue and perennial ryegrass.

8. A seed or tissue derived from the plant of claim 6 wherein said seed or tissue each comprises the introduced gene encoding tyramine N-(hydroxycinnamoyl)transferase.

* * * * *

SEQUENCE LISTING

```
<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: primer for PCR of a THT gene isolated from
      Capsicum annuum

<400> SEQUENCE: 1
atcaagctta tggcttctgc tcctcaa                                           27

<210> SEQ ID NO 2
<211> LENGTH: 27
<212> TYPE: DNA
<213> ORGANISM: Artificial Sequence
<220> FEATURE:
<223> OTHER INFORMATION: primer for PCR of a THT gene isolated from
      Capsicum annuum

<400> SEQUENCE: 2
gtggagctcc taacagcttc ctgcacc                                           27

<210> SEQ ID NO 3
<211> LENGTH: 753
<212> TYPE: DNA
<213> ORGANISM: Capsicum annuum
<220> FEATURE:
<221> NAME/KEY: gene
<222> LOCATION: (1)..(753)
<223> OTHER INFORMATION: a full-length THT gene isolated from
      Capsicum annuum

<400> SEQUENCE: 3
atggcttctg ctcctcaacc accaactcta tctgaaaaaa ccactaatct ctcaccggaa        60
aacgacaatg ttacgatcac cggaaagata tatacaagag tccgccttgc tacaaaatct      120
gatctgcacc atgcatacca gttgttttac caaatccacg cataccataa ccaatttcat      180
ttattcaaag caacagagtc ctccttatcg gacttgttct ttaaagaaaa tcctcttccc      240
cttttctacg gaccaaccct acttctactc gaagtctccc cgaccgcttt tactgaaccc      300
aaaaataaca aggacgaagg gttcaaaccc gtctttacag cgctcgacct taaatttcct      360
gtcgtggaag gacaagttga ggagtttcgg tccaaatatg atgatggaac cgataaacgt      420
gatgtgttca tcgcgggata tgcttacttt tttgctagtt attcactctt cgggaacgac      480
aaaccgggga tccatttcga cagtctttac ttcagggaaa gctatagaaa attgggaatg      540
ggaaaattgt tgtttggaac tgttgcgtct attgctgcga acaatgggtt tgctgcggtg      600
gagggaattg tagcagtttg gaataaaaag tcatatgatt tttatgtgag tatgggtgtt      660
gaaatgcatg atgactttag gtttggcaaa ttggacggtg aaaatcttca aaagtacgct      720
gataaggaga aaaatggtgc aggaagctgt tag                                    753
```